United States Patent [19]

Suzuki et al.

[11] Patent Number: 4,997,645

[45] Date of Patent: Mar. 5, 1991

[54] METHODS AND PHARMACEUTICAL COMPOSITION FOR THE TREATMENT OF TUMORS

[75] Inventors: Nobuo Suzuki, Funabashi; Yoshiaki Takakubo, Shizuoka, both of Japan

[73] Assignee: Boehringer Ingelheim GmbH, Ingelheim am Rhein, Fed. Rep. of Germany

[21] Appl. No.: 207,622

[22] Filed: Jun. 16, 1988

[30] Foreign Application Priority Data

Jun. 16, 1987 [EP] European Pat. Off. ........ 87108708.6

[51] Int. Cl.$^5$ ............................................. A61K 37/66
[52] U.S. Cl. ................................. 424/855; 424/85.4; 424/85.6; 424/85.7
[58] Field of Search ............ 424/85.4, 85.5, 85.6, 424/85.7

[56] References Cited

U.S. PATENT DOCUMENTS 3,031,450  4/1962  Fischer et al.

FOREIGN PATENT DOCUMENTS 0084953  1/1983  European Pat. Off.

OTHER PUBLICATIONS

Goldstein et al., Career Research, vol. 46, pp. 4315–4329, 1986.
Grem et al., Chem. Abstr. 103:30 (1985).
Grem et al., Cancer Res. 45:2967–2972 (1985).
European Search Report for the corresponding European patent application.
H. Gastpar, Laryngol Rhinol Otol (Stuttg), 62(12):578–85, Dec. 1983 (abstract).
Slichter, S. J., et al., Blood, 59(6):1252–8 (Jun., 1982), abstract.
Chan et al., Canc. Treat. Reports 69:425 (1985).
Chan et al., Canc. Res. 43:3598 (1985).
Zhen et al., Canc. Res. 43:1616 (1983).
Nelson et al., Canc. Res. 44:2493 (1984).
Weber, Canc. Res. 43:3466 (1983).
Bastida et al., Canc. Res. 45:4048 (1985).
Ambrus et al., Proc. Amer. Assoc. Canc. Res. 23:189 (1982).
Biddle et al., Proc. Soc. Exp. Biol. Med. 197:487 (1982).
Wolf et al., J. Med. 15:15 (1984).
Chervinsky et al., Proc. Amer. Assoc Canc. Res. 24:309 (1983).
Galabov et al., Acta Virol. 26:137 (1982).

Primary Examiner—Blondel Hazel
Attorney, Agent, or Firm—Saidman, Sterne, Kessler & Goldstein

[57] ABSTRACT

Disclosed is a method of treating tumors capable of being treated with interferon which is comprised of interferon and dipyridamole, or pharmaceutically acceptable salts thereof, in amounts sufficient to enhance the anti-tumor effect of interferon. Further disclosed is a pharmaceutical composition comprised of interferon and dipyridamole.

21 Claims, 11 Drawing Sheets

FIG. 1  TIME IN CULTURE (DAYS)

METHODS AND PHARMACEUTICAL COMPOSITION FOR THE TREATMENT OF TUMORS

BACKGROUND OF THE INVENTION

1. Field of the Invention

The present invention relates generally to the treatment of tumors, in particular the treatment of tumors using an interferon. More specifically, the invention relates to the use of dipyridamole for enhancing the tumor-growth inhibitory action of an interferon, a method of treating a patient suffering from a tumor by combined therapy with dipyridamole and an interferon, the use of dipyridamole and interferon for preparing such pharmaceutical preparations for treating tumors, and to pharmaceutical preparations so produced.

2. Brief Description of the Background Art

Information on the inhibitory action of human interferon (HuIFN) on the growth of cultured cell lines has been accepted as viable for clinical trials of HuIFN as antitumor therapy (*Adv. Cancer Res.*, Vol. 46, Academic Press. London (1986), and Stewart, *The Interferon System*. Springer-Verlag, Wien/New York, (1981).

Recently, it has been found that the susceptibility of human cells to the anticellular effects of HuIFN correlated with radio-sensitivity and/or DNA-repair capacity. Suzuki et al., *Virology*. 135:2029, (1984); *Mutation Res.*, 106:357-376, (1982); *J. Gen. Virol.*, 67.651-661 (1986), Yarosh et al., *Carcinogenesis* 6:883-886 (1985) *Biophys. Res. Commun.*, 72:732 (1976). It has also been found that the cellular response mechanisms for DNA damage are modified by HuIFN treatment itself; for example, the increase of DNA-repair synthesis levels and enhancement of survival of cells treatment with agents which can cause structural damage of DNA. Suzuki et al., *Virology*, 135:20-29, (1984); *Mutation Res.*, 175: 189-193 (1986). Therefore, it seems undesirable to carry out antitumor therapy by HuIFN in combination with other anti-cancer agents which damage DNA because of HuIFN induced resistance to the agents, and there is a need for an agent which does not itself cause DNA damage but can enhance the antitumor activity of interferon.

The compound 2,6-bis(diethanolamine)-4,8-dipiperidino-pyrimido[5,4-d]pyrimidin, which has the generic name dipyridamole, and its preparation have been described in U.S. Pat. No. 3,031,450.

Dipyridamole is a well known vasodilator and also has platelet aggregation inhibiting properties. In view of these properties, it has found widespread use for many years in the treatment of chronic coronary insufficiency and in the prophylaxis and treatment of heart infarcts as well as in the prophylaxis of arterial thrombosis.

More recently, the possible use of dipyridamole in tumor therapy has been investigated. This interest has derived from the observation that while it does not damage DNA, dipyridamole is an effective blocker of the salvage pathway of DNA synthesis, and that it can inhibit nucleoside transport through the cell membrane and so block restoration of internal cellular nucleoside levels, thus potentially inhibiting important steps in tumor cell synthesis. *Biochem. Biophys. Acta*, 58:435-447, (1968), and *Biochem. Biophys. Acta*. 219:88-94, (1970).

In view of this property, the effects of dipyridamole, both alone and in combination with various anti-cancer agents, have been investigated. Thus, Chan et al., *Cancer Treat. Rep.*, 69:425-430, (1985) found that dipyridamole can potentiate the activity of N-phosphoracetyl-L-aspartate (PALA) *in vitro* and *in vivo*. PALA is a pyrimidine anti-metabolite which is thought to inhibit an early step in *de novo* pyrimidine synthesis, causing depletion of intracellular pyrimidine nucleotides. In another study Chan et al., *Cancer Research*, 45:3598-3604 (1985) reported that dipyridamole increased PALA activity against a human ovarian carcinoma cell line while exhibiting no cytotoxicity of its own.

Zhen et al., *Cancer Research*, 43:1616-1619, (1983), reported that the addition of a combination of cytidine, deoxycytidine and guanosine at an optimal concentration of 8 $\mu$M each protected rat hepatoma 3924 A cells from the growth-inhibitory action of the antiglutamine drug Acivin, and that this protection was blocked by dipyridamole at a concentration of 6 $\mu$M.

Nelson et al., *Cancer Research* 44: 2493-2496, (1984) reported that dipyridamole enhanced the toxicity of methotrexate (MTX) towards chinese hamster ovary cells both *in vitro* and *in vivo*: however, the antitumor activity of MTX towards certain other tumors, namely ridgway osteogenic sarcoma and L1210 leukemia was not dramatically improved.

Various other publications describe the testing of dipyridamole together with anti-cancer agents against tumor cells, e.g. with cytarabine (*Cancer Treat. Rep.* 68: 361-366, (1984) and 2'-deoxyadenosine (*Cancer Research* 45: 6418-6424, (1985)

In addition, some investigations have been carried out on the use of dipyridamole alone as an anti-cancer drug. Thus, in the investigation on the combined action of dipyridamole/acivin, Weber, *Cancer Research* 73: 3466-3492, (1983), also showed that dipyridamole was effective in killing Hepatoma 3924A cells. Bastida, *Cancer Research* 45: 4048-4052, (1985), reported a potential metastatic effect of dipyridamole, possibly resulting from inhibition of tumor cell metabolism or suppression of one or more of the mechanisms involved in the ability of tumor cells to activate platelets.

Work has also been carried out on the structurally related compound 2,6-bis-(diethanolamino)-4-piperidino-pyrimido[5,4-d]pyrimidine (Mopidamole) as an anti-cancer drug.

Gastpar, *Laryng. Rhinol. Otol.* 62: 578-525 (1983) reported that mopidamole potentiates the antimitotic effect of interferon and its natural killer cell activating activity. He reports in the same article that ' the adding of mopidamole to a culture of a human promyelocytic leukemic cell line promotes a reverse transformation of malignant cells to normal which appears to be a permanent phenotypic change. Furthermore, mopidamole was shown to diminish significantly spontaneous lung metastases in syngeneic Wilms Tumor (nephroblastoma) of the rat, the C1300 neuroblastoma of the mouse and the HMKim mammary carcinoma of the rat.'

The use of mopidamole in the above investigation was based on its ability to increase cAMP levels, resulting in an inhibition of 3Hthymidine incorporation into neoplastic cells and a direct inhibition of the mitotic rate. The effect on cAMP levels derives from mopidamole's inhibition of PDE induced decomposition of cAMP, it may also stimulate the synthase and/or release of prostacyclin from the vessel wall which in turn activates adenylate cyclase involved in cAMP synthesis. Dipyridamole is, however, known to be much weaker PDE inhibitor than mopidamole.

It must also be observed that the teaching in the literature of the combination of mopidamole with interferon is confusing. Ambrus, J.L. et al. Proc. Am. Assoc. Cancer Res. 23: 183 (1932) state that mopidamole potentiates the antitumor effect of leukocyte and fibroblastic interferon in tissue culture, and in Proc. Soc. Exp. Biol. Med. 177: 487-490 (1984) state that mopidamole potentiates the growth inhibitory effect of human fibroblastic $\beta$-interferon. Wolf et al., J. MED. 15-21 (1984) concludes that, in contrast to its effect with human fibroblast interferon, no synergistic inhibitory effect between mopidamole and a variety of $\alpha$ and $\gamma$ interferon could be observed. Finally, Ambrus et al. Proc. Am. Assoc. Cancer Res. 24: 309 (1983) state that, in contrast to some previous reports, no synergism was seen between interferon and mopidamole.

Galabov et al. Acta. Virol. 26 (3): 137-174 (1982) described a investigation with dipyridamole. European Patent Application 0.084.953. Galabov et al. reported that dipyridamole induced interferon production in vitro in explanted mouse peritoneal leukocytes and other cells and it induced interferon in mice after I.V. administration. However, this work has not been confirmed by other groups.

It is no where taught or suggested in the literature either to use dipyridamole in combination with an interferon in antitumor therapy, or suggested that any worthwhile results could be expected from such a combined therapy.

BRIEF DESCRIPTION OF FIGURES

FIG. 2
Morphology and cell distribution 6 days after continuous exposure to HuIFN-$\beta$ and dipyridamole in MM-1CB. (A) mock HuIFN-$\beta$ corresponding to 10 units/ml HuIFN-$\beta$, (B) 0.1 $\mu$M dipyridamole, (C) 10 units/ml HuIFN-$\beta$, (D) 10 units/ml HuIFN-$\beta$ and 0.1 $\mu$M dipyridamole.

FIG. 3
(A) Cell survival percents 6 days after continuous exposure to 0.1 $\mu$M dipyridamole and various units of HuIFN$\alpha$($\triangle$ and $\blacktriangle$), -$\beta$(o and $\bullet$) and -$\gamma$($\square$ and $\blacksquare$) in MM-1CB. $\triangle$, $\bigcirc$, and, treatment with HuIFN alone; $\blacktriangle$, $\bullet$ and $\blacksquare$, treatment with HuIFN and dipyridamole.

(B) Cell survival percents 6 days after continuous exposure to units/ml HuIFN-$\alpha$ ($\blacksquare$), $\beta$($\bullet$) and -$\gamma$($\blacksquare$) in combination with various concentrations of dipyridamole in MM-1CB. $\bigcirc$,, treatment with dipyridamole alone.

FIG. 4
(A) Cell survival percents 4 days after continuous exposure to 0.1 $\mu$M and various units of HuIFN-$\alpha$ in KT cells. $\bigcirc$ treatment with HuIFN-$\alpha$ alone; $\bullet$, treatment with Hu IFN-$\alpha$ and dipyridamole.

(B) Cell survival percents 4 days after continuous exposure to 10 units/ml HuIFN-$\alpha$ and various concentrations of dipyridamole. $\bigcirc$, treatment with dipyridamole alone; $\bullet$, treatment with HuIFN-$\alpha$ and dipyridamole.

FIG. 5
(A) cell survival percents 6 days after continuous exposure to 0.1 $\mu$M and various units of HuIFN-$\beta$ in PLC/PRF/5 cells. $\bigcirc$, treatment with HuIFN-$\beta$ alone; $\bullet$, treatment with HuIFN-$\beta$ and dipyridamole. $\triangle$ (B) Cell survival percents 6 days after continuous exposure to 10 units/ml HuIFN-$\beta$ and various concentrations of dipyridamole. $\bigcirc$, treatment with dipyridamole alone; $\bullet$ treatment with HuIFN-$\beta$ and dipyridamole.

FIG. 6
Morphology and cell distribution 2 days after exposure to HuIFN-$\alpha$ and dipyridamole in KT cells. (A) Control, (B) 0.1 $\mu$M dipyridamole, (C) 10 units/ml HuIFN-$\alpha$, (D) 10 units/ml HuIFN-$\alpha$ and 0.1 $\mu$M dipyridamole.

FIG. 7
Morphology and cell distribution 6 days after exposure to HuIFN-$\beta$ and dipyridamole in PLG/PRF/5 cells. (A) Control, (B) 0.1 $\mu$M dipyridamole, (C) 10 units/ml HuIFN-$\beta$, (D) 10 units/ml HuIFN-$\beta$ and 0.1 $\mu$m dipyridamole.

SUMMARY OF THE INVENTION

The present inventors have found that dipyridamole, a compound which does not have DNA damaging properties, or a pharmacologically acceptable salt thereof, unexpectedly enhances the anti tumor effect of an interferon chosen from HuIFN$\alpha$, $\beta$ or $\gamma$.

Accordingly, a first aspect of the present invention comprises the treatment of a patient suffering from a tumor which comprises administering dipyridamole, or a salt thereof, to the patient in an amount sufficient to enhance the antitumor effect of an interferon which is also administered to the patient.

A second aspect of the invention comprises a method of treating a patient suffering from a tumor, which comprises administering an interferon and dipyridamole, or a pharmaceutically acceptable salt thereof, to said patient, the dipyridamole or salt being administered in an amount which enhances the antitumor effect of the interferon.

A further aspect of the invention comprises dipyridamole or a pharmaceutically acceptable salt thereof for the manufacture of a pharmaceutical composition suitable for enhancing the antitumor effect of an interferon when administered to a patient suffering from a tumor and to whom said interferon is also administered.

Yet a further aspect of the present invention comprises an interferon for use in manufacturing a pharmaceutical composition for use together with dipyridamole or a pharmaceutically acceptable salt thereof in the treatment of a tumor, whereby said dipyridamole or salt is used to enhance the antitumor effect of said interferon.

Another aspect of the present invention comprises a pharmaceutical composition containing an interferon and dipyridamole or a pharmaceutically acceptable salt together with conventional pharmaceutical excipients.

DESCRIPTION OF THE PREFERRED EMBODIMENTS

The term interferon, as used herein, means any of the leucocyte ($\alpha$), fibroblast ($\beta$) or immune ($\gamma$) interferons.

The amino acid sequences of the various interferons, their preparation by recombinant technology and the preparation of pharmaceutical compositions containing them are described in the literature.

For example, the amino acid sequence and recombinant preparations of HuIFN$\alpha$2b is described in European Patent Publication No. 0.043.98; for HuIFN$\alpha_2$b) in European Patent Publication No. 0.32.134, and for HuIFN$\alpha_2$c in European Patent Publication No. 0.115.613. Similarly, European Patent Publication No. 0.028.033 describes the amino acid sequence and production by recombinant techniques of HuIFN-$\beta$. The amino acid sequence and recombinant preparation of HuIFN-$\gamma$ is described in European Patent Publication No. 0.051.873.

The dipyridamole or salt thereof and interferon must be administered such that they are simultaneously present at the tumor site. Preferably, therefore, they are administered simultaneously or substantially simultaneously. The term "substantially simultaneously" means "at about the same time" with the only limitation being that both substances must be present together at the tumor site. In any given case, the coordination of the administration of the interferon and dipyridamole so that this limitation is met, will be determined according to the pharmacokinetics of the compound which will be known to persons of ordinary skill in the art of the invention. It is presently considered that the preferred effective plasma level of dipyridamole for the antitumor treatment is about 0.1 $\mu$M (50 ng/ml) and the effective plasma level of interferon for the treatment about 10 I.U./ml.

The recommended dosages for both dipyridamole and its salt and the interferons are based on the above proposed plasma levels. It will be clear that actual dosages may be altered by the attending physician depending upon the circumstances and conditions of the individual patient.

For the present invention, the interferon may be administered by parenteral route. The dosage and dosage rates are preferably about $1 \times 10^6$ to $10 \times 10^6$ I.U., preferably $1 \times 10^5$ to $1 \times 10^6$ I.U. given twice daily in the case of intravenous administration and once daily in the case of intramuscular injection.

The preparation of suitable dosage forms for human interferons is well known.

To produce a convenient dosage form for parenteral use, an appropriate amount of HuIFN may be dissolved in 5% human serum albumin, if necessary containing suitable buffer solution. This resulting solution is then passed through a bacteriological filter and the filtered solution is distributed between vials under aseptic conditions, each vial containing an appropriate amount of the interferon and, if desired, lyophilized. The glass vials are preferably stored under cool conditions ($-20°$C.) before use. The interferons may be formulated in known manner in order to obtain pharmaceutically usable compositions, the interferon being mixed with a pharmaceutically acceptable carrier substance; conventional carriers and their formulation are described by E.W. Martin in *Remington's Pharmaceutical Sciences*, which is herein incorporated by reference.

The dipyridamole or salt thereof can be administered by any of the usual routes of administration, for example, orally or parenterally. At present, the preferred route of administration is oral. The recommended dosages are 25 to 100 mg, preferably 30 to 60 mg twice daily. However, if desired, 10 to 20 mg of dipyridamole may be used as one dose, being administered intravenously in one hour together with interferon.

Dipyridamole is commercially available under the trademark Persantin ™ in a number of forms. For instance, injection solution containing 10 mg dipyridamole and dragees containing 25 mg and 75 mg dipyridamole are described in the Rote Liste 1987 published by the Bundesverband der Pharmazeutischen Industrie e.V., D-6000 Frankfurt a.M., West Germany. Suitable dosage forms containing various amounts of dipyridamole can be prepared using standard techniques. In addition, a number of special galenic forms have been described in the literature which are aimed at providing either accelerated or delayed (sustained) release and resorption of dipyridamole, such as the retard capsule form described in European Patent Publication No. 0.032.562 and the instant release form described in European Patent Publication No. 0.068.191. A further delayed release galenic form is described in British Patent No. 2.025.227.

The present invention is predicated on the observation that in various established human cell lines, dipyridamole demonstrated the surprising property of enhancing the growth inhibition effects of various human interferons. Studies conducted to test this observation are described below:

Four established cell lines were used. These were MM-1CB, derived from tissues of malignant melanoma (level IV, pT4N$_0$M$_0$) in a 70-year-old man (*Jon. J. Dermatol.* 96:947 (1986)); KT, derived from metastatic brain tumor in a 52-year-old woman (*J. Rad. Res.* 26:59 (b 1985) and The 44th Meeting of Japanese Cancer Association, 718 (1985)); PLC/PRF/5, derived from human hepatoma (*Brit. J. Cancer* 34:509-515 (1976)) and a transformed cell line RSa (*Virology* 135:20-29 (1984), and *J. Natl. Cancer Inst.* 56:919-926 (1976)).

Cells were cultured with Eagle's minimal essential medium (EMEM) containing 10% fetal bovine serum (GIBCO, U.S.A.) and antibiotics (100 $\mu$g streptomycin/ml and 100 units penicillin G/ml), in an incubator at 37° C. under 5% CO$_2$.

Natural HuIFN preparations: $\alpha$ ($10^8$ internatioanl reference units (I.U.)/mg protein), $\beta$($10^7$ I.U./mg protein) and mock $\beta$, and $\gamma$($10^6$) I.U./mg protein), were purchased from ENZO BIOCHEM INC. (U.S.A.), Flow-Rentschler Inc. (W. Germany) and Paesel GmbH & Co. (W. Germany). Dipyridamole and Mopidamole were provided by Boehringer Ingelheim GmbH (W. Germany). Other chemical agents were purchased from the Nakarai Co., Ltd., Japan.

Cell Proliferation Inhibition Test

Logarithmically growing cells of each cell line were seeded: $1-5 \times 10^4$ cells per one 60-mm dish (IWAKI, Japan), and 20 hours after the seeding, were washed and re-fed with the medium containing HuIFN preparations and dipyridamole with or without dipyridamole. Changes of medium with and without agents were carried out every other day. The viable cells were determined by trypan-blue exclusion test and counted with a hemocytometer. The survival percentage ratio was expressed as (counts of viable cells in test dishes per counts of viable cells in control dishes) ×100%, as described elsewhere in, e.g., *Mutation Research* 106:357-376 (1982) and *J. Gen. Biol.* 67:651-661 (1986).

DNA Synthetic Activity Test

[($^3$H]dTHD uptake into acid insoluble materials were estimated in KT and RSa cells treated with the various agents, as described in *J. Gen. Virol.* 67:651-661 (1986).

Microscopic Study

Cells seeded in test dishes were observed and photographed using OLYMPUS IMT-2 (×100 - ×1500 amplification).

Most of experiments were carried out under a dim light or in the dark. Results were expressed as the mean of values obtained from more than two independent experiments.

Figure 1:
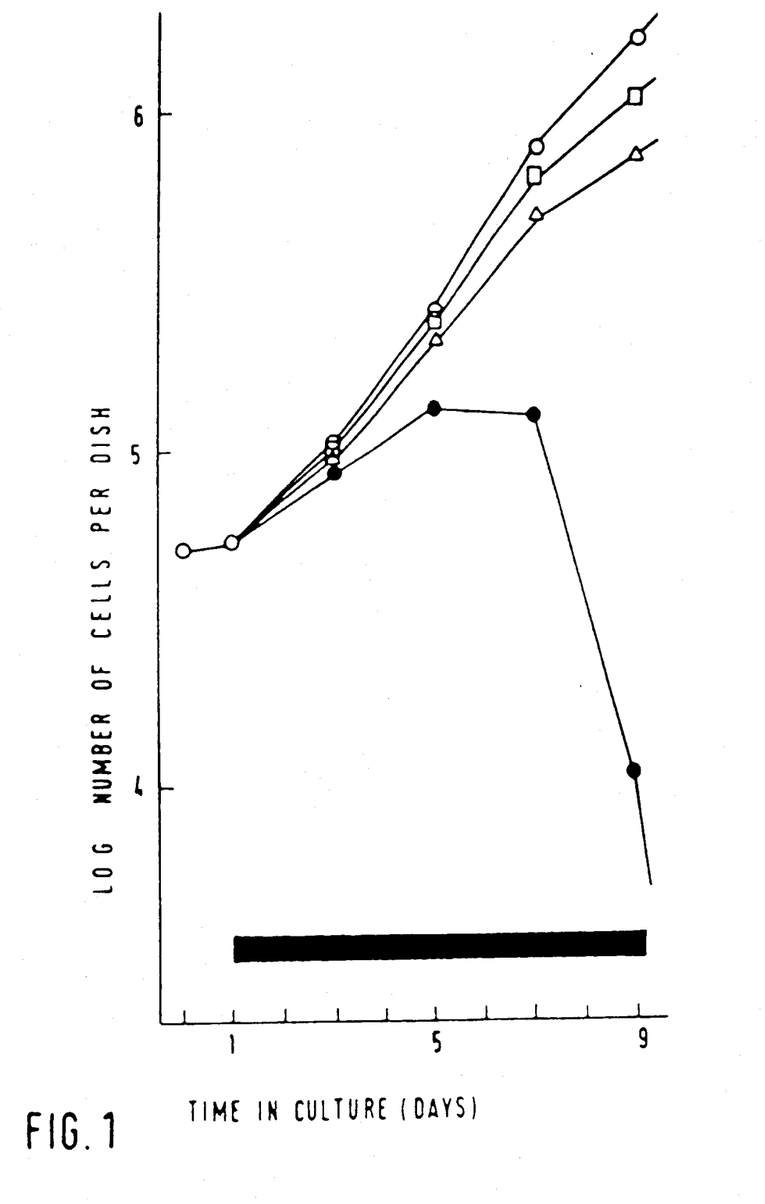
FIG. 1
Growth curves of MM-1CB. $\bigcirc$, treatment with mock HuIFN-$\beta$ corresponding to 10 units/ml HuIFN-$\beta$: $\square$, treatment with 0.1$\mu$M dipyridamole; $\triangle$, treatment with 10 units/ml HuIFN-$\beta$ $\bullet$, with 10 units/ml HuIFN-$\beta$ and 0.1 $\mu$M dipyridamole. $\blacksquare$, period of treatment with drugs.
Figure 2A:
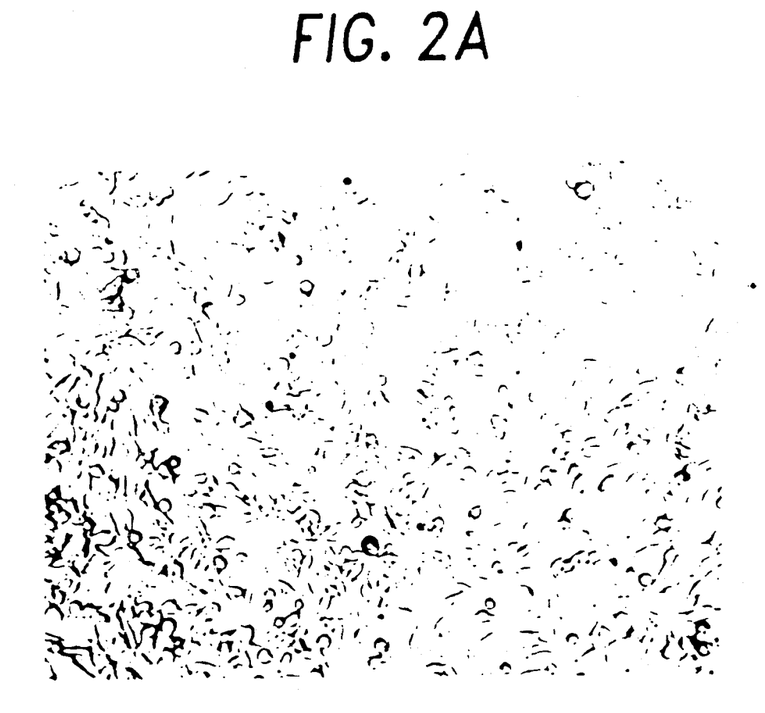
Figure 2B:
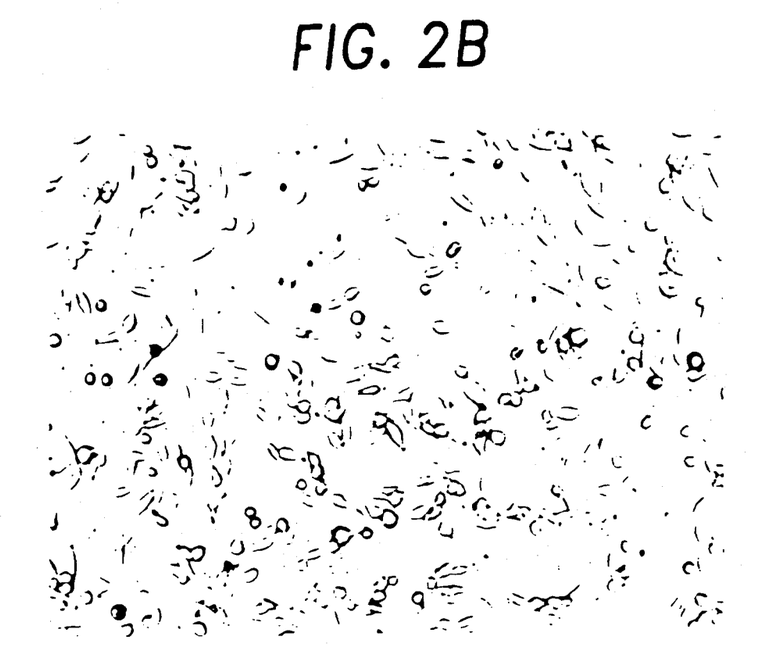
Figure 2C:
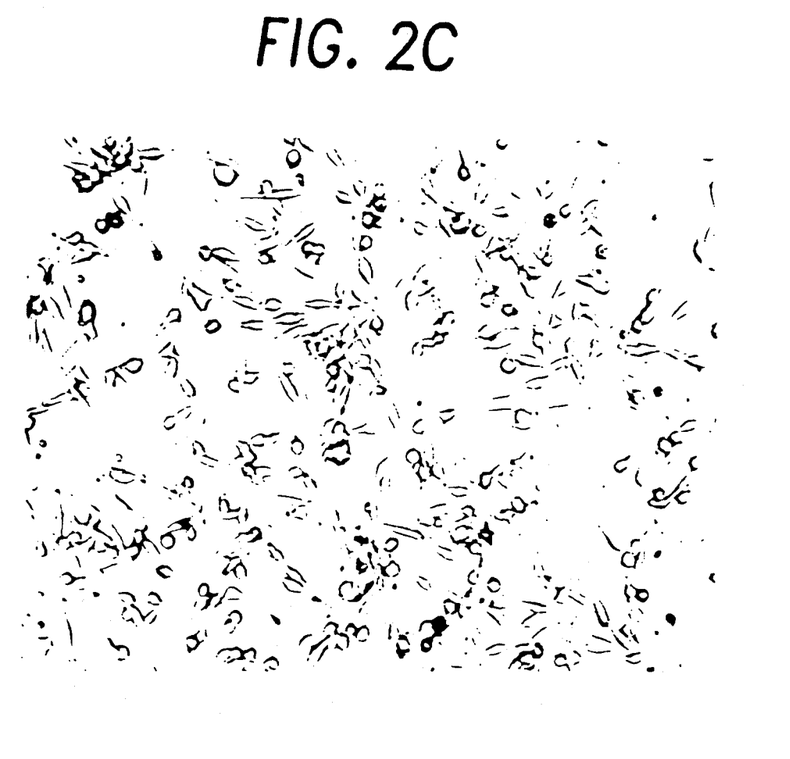
Figure 2D:
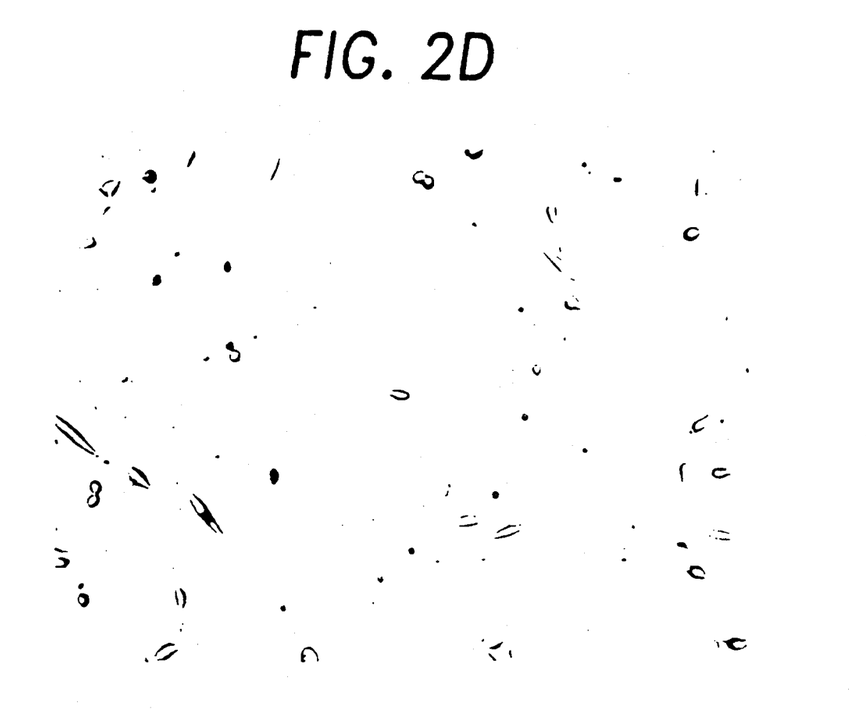
Figure 3A:
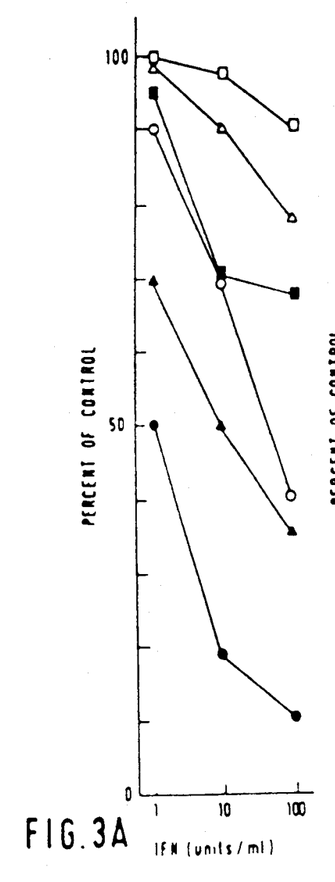

In the investigation on MM-ICB cells treatment with either agent alone, 10 units/ml HuIFN-β or 0.1 μM dipyridamole, was only slightly effective in suppressing cell proliferation, whereas considerable inhibition of cell growth was evident upon treatment of the cells with both these agents together for more than 4 days (FIG. 1). After the combined treatment, the cells appeared morphologically impaired in comparison with cells treated with mock HuIFN-β, whereas cells treated with each agent alone did not (FIG. 2). When the cells were treated continuously with 0.1 μM dipyridamole, the additive effect with HuIFNα, −β and γ was also observed (FIG. 3A). Higher concentrations and even lower concentrations down to 0.01 μM of dipyridamole were effective in enhancing the anticellular effect of HuIFN (FIG. 3B).

Figure 4A:
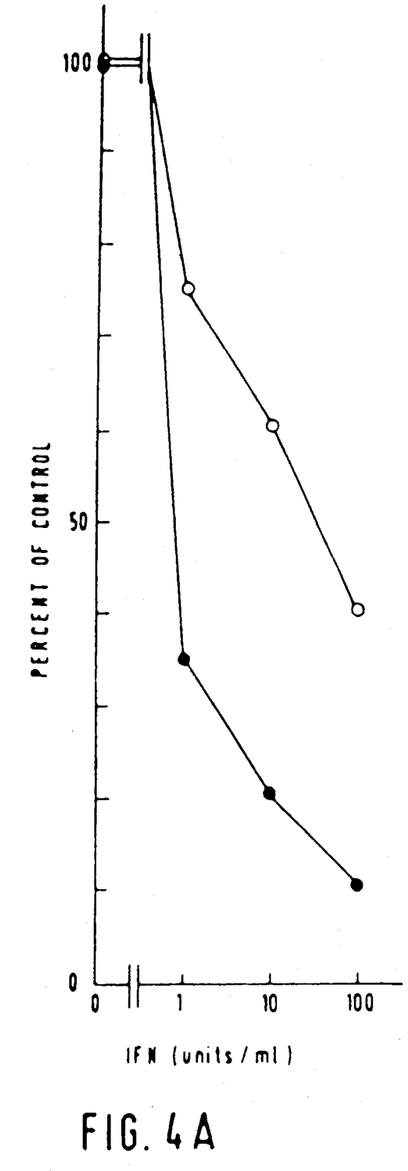
Figure 4B:
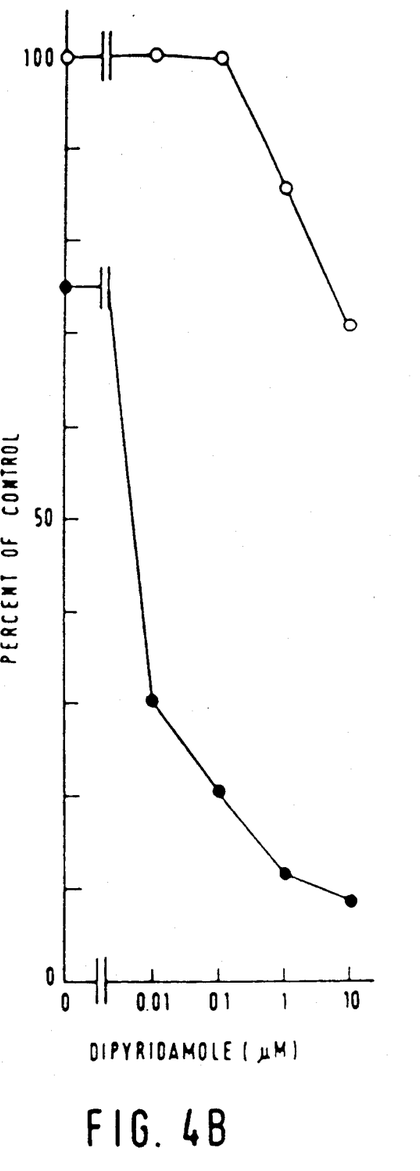
Figure 5A:
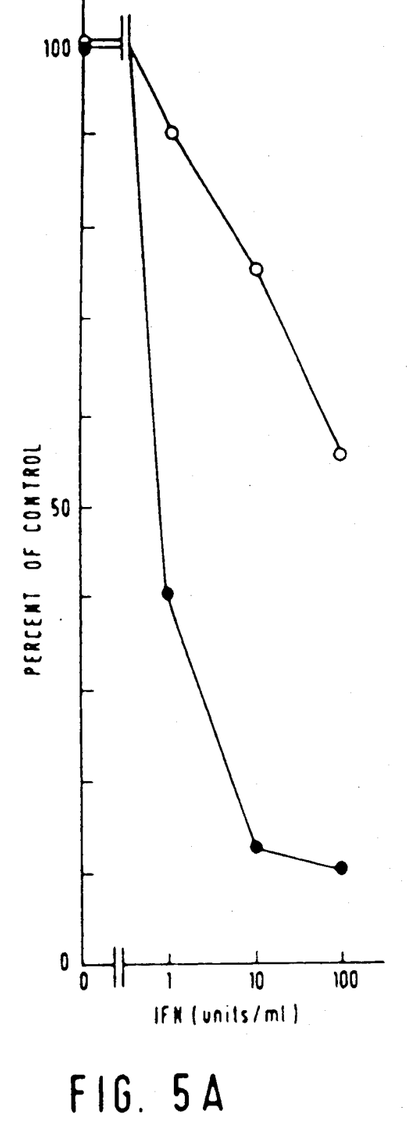
Figure 5B:
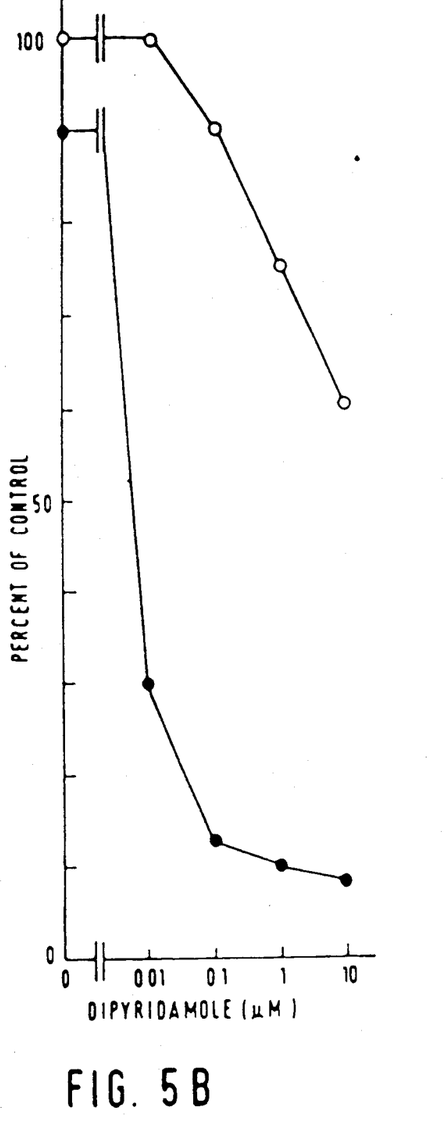
Figure 6A:
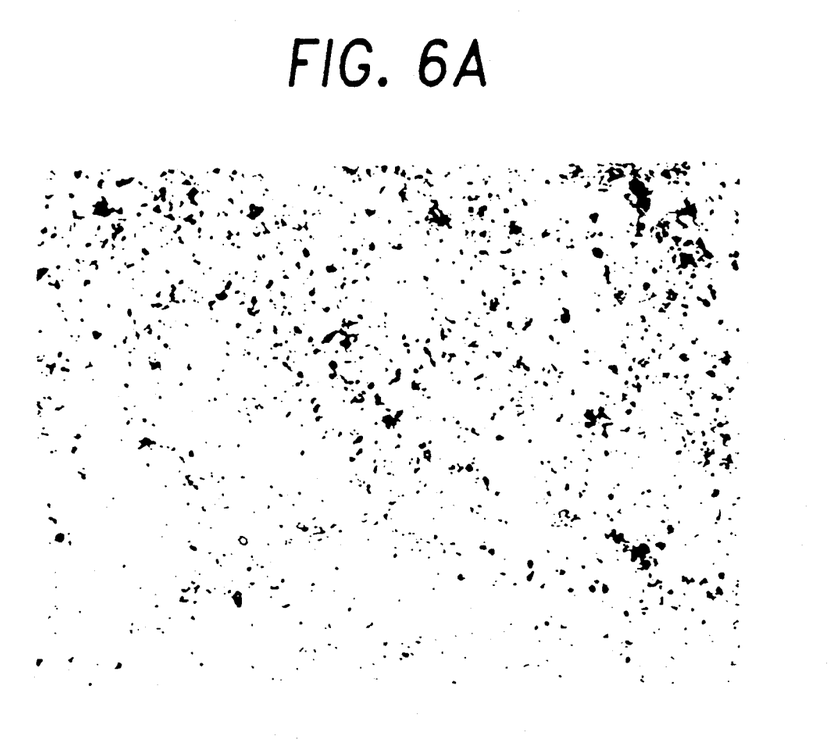
Figure 6B:
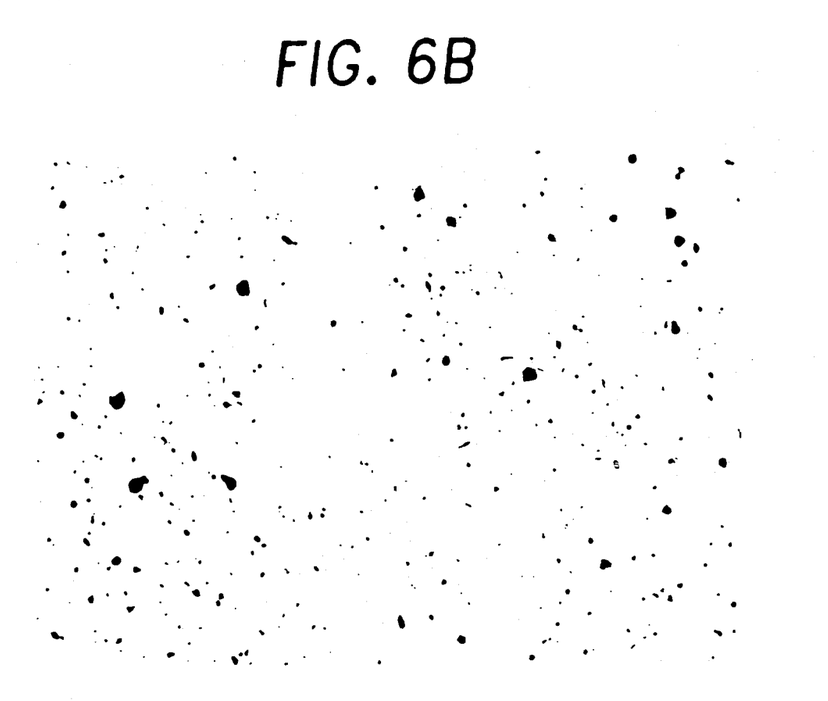
Figure 6C:
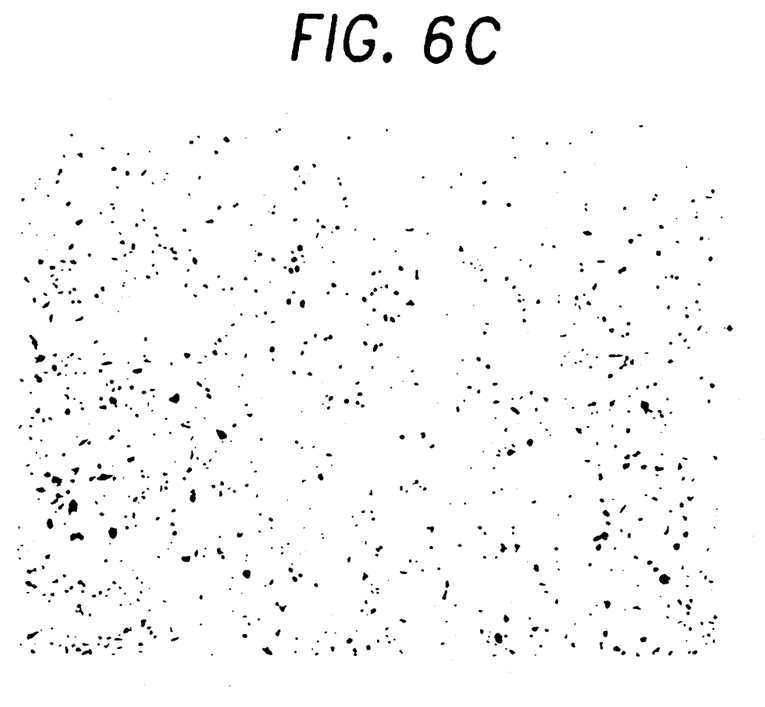
Figure 6D:
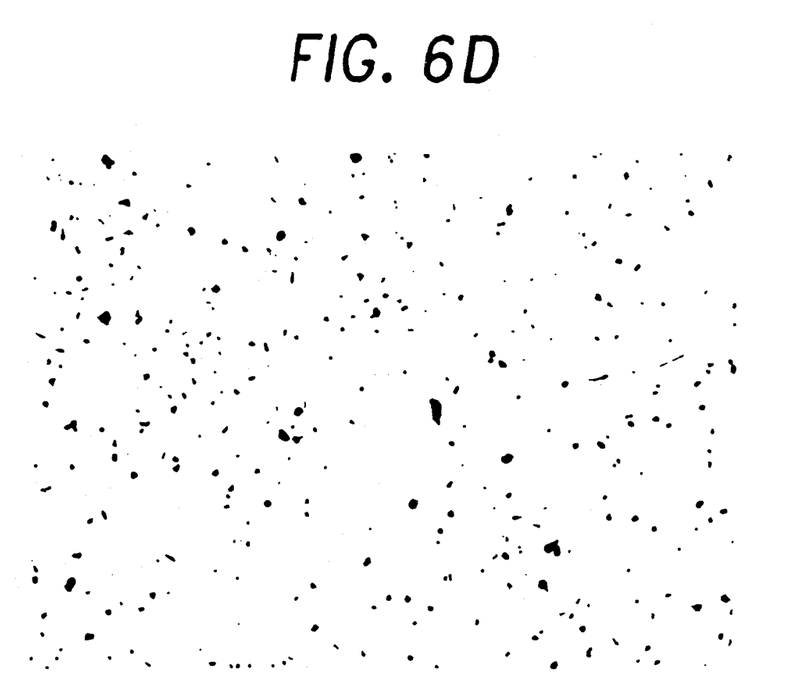
Figure 7A:
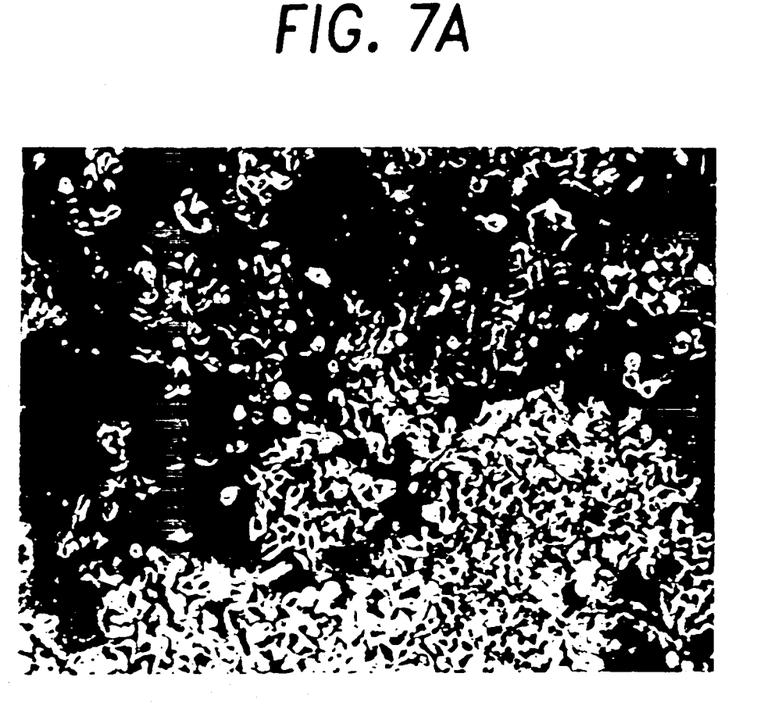
Figure 7B:
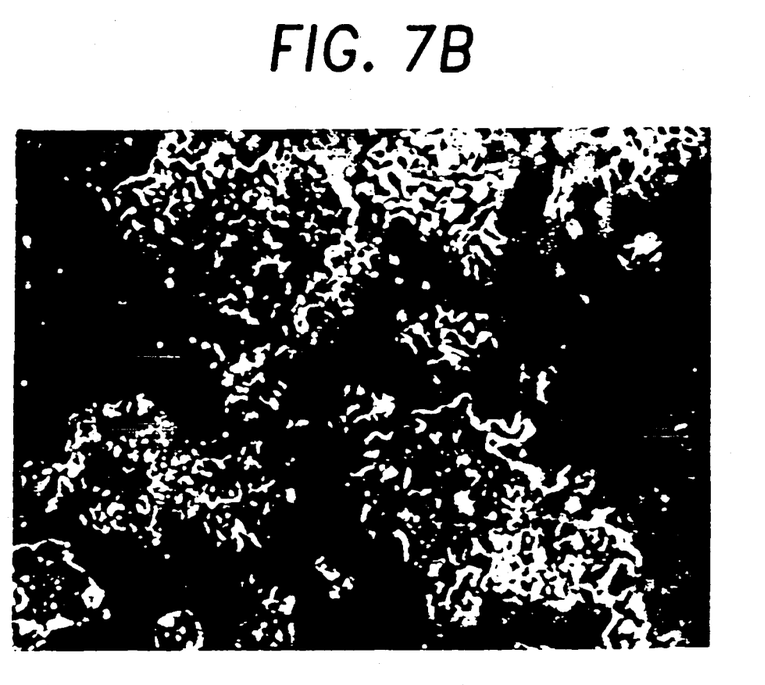
Figure 7C:
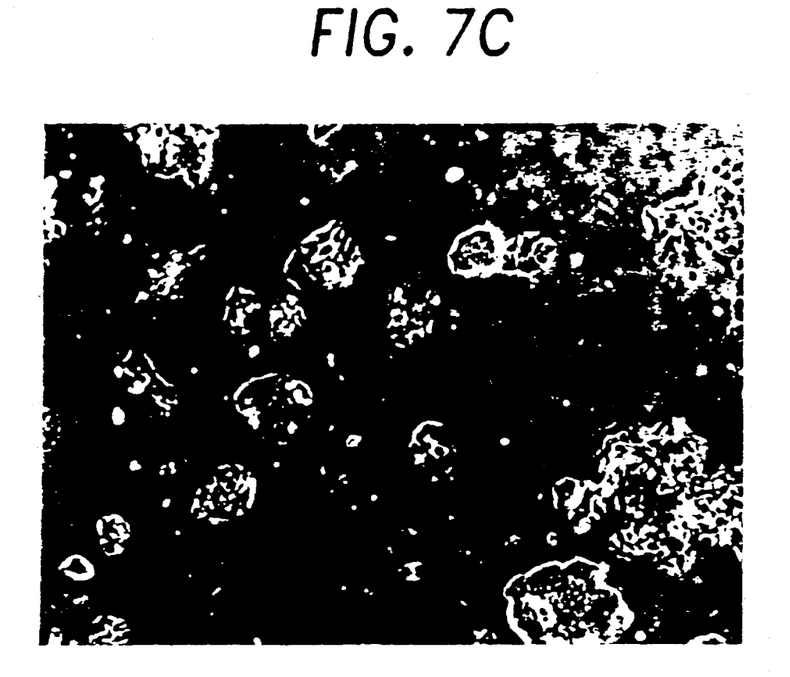
Figure 7D:
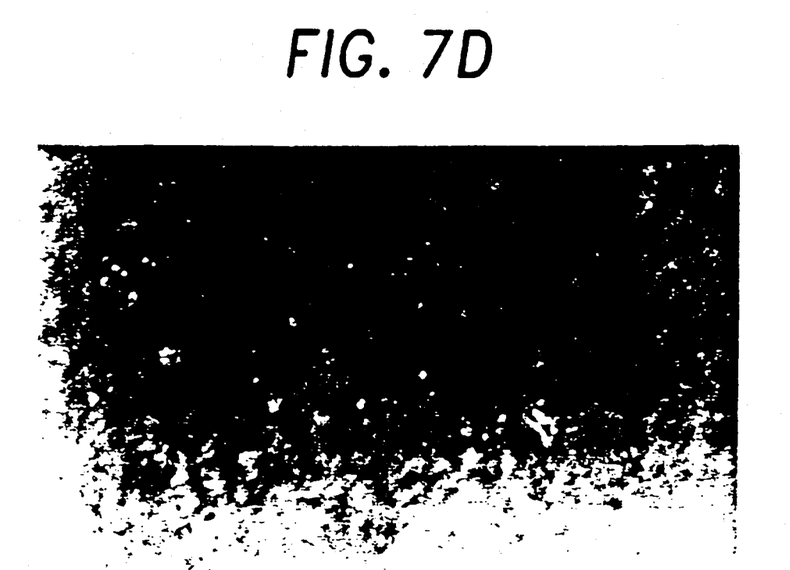

When the other two cell strains: metastatic brain tumor (KT) and hepatoma (PLC/PRF/5) cell lines, were treated with HuIFN and dipyridamole, both cells showed high susceptibility to the synergistic inhibitory activity (FIGS. 4 and 5). Although cell replication of KT cells was greatly inhibited by HuIFN-α, the inhibition of cell replication was enhanced in comparison with the simultaneous exposure to dipyridamole (FIG. 4). Even less than 0.1 μM dipyridamole, at concentration dipyridamole alone, which scarcely influenced KT cell replication, could enhance the inhibitory effect of HuIFN-α (FIG. 4B). It was evident that cellular morphological conditions of both cell strains also showed impairment after the combination treatment (FIGS. 6 and 7).

Figure 3B:
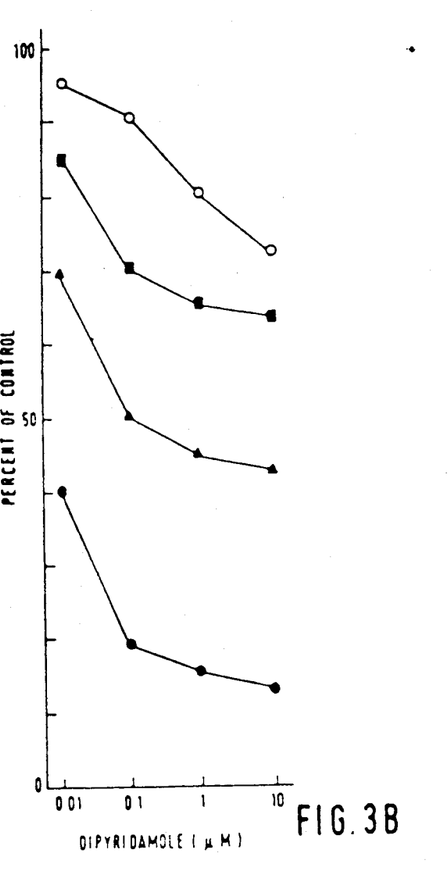

The concentration of dipyridamole in blood during the several hours after its administration is a few micromoles, whereas the present inventors found the most effective concentration for the synergistic enhancement of HuIFN action was much less, i.e., less than 0.1 μM (FIGS. 3B, 4B and 5B). Results in FIGS. 3A, 4B and 5B revealed that very low unit concentration of HuIFN (less than 10 units/ml) was also effective for the anticellular action even when applied in combination with low concentrations of dipyridamole. Therefore, dipyridamole may also enable a reduction in the dosage of HuIFN in the treatment of tumor.

IFN-susceptibility varies among different cell types (Strander et al., *Adv. Cancer Res.*, Academic Press, London, 46 (1986); Stewart II, *The Interferon System*, Springer-Verlag, Wien/New York (1981); Yarosh et al., *Carcinogenesis* 6:883-886 (1985)); but there exists positive correlation between the survival susceptibility and DNA-synthesis levels in the treated cells (Suzuki et al., *J. Gen. Virol.* 67:651-661 (1986)). Estimation of DNA-synthesis level is a useful method for evaluating IFN-susceptibility and, further, requires no more time than does the cell proliferation inhibition test used here. Therefore, the synergism found was also confirmed by the DNA-synthesis levels in KT and RSa, well known to be highly sensitive to HuIFN (Suzuki et al., *J. Gen. Virol.* 67:651-661 (1986)).

Figure 8:
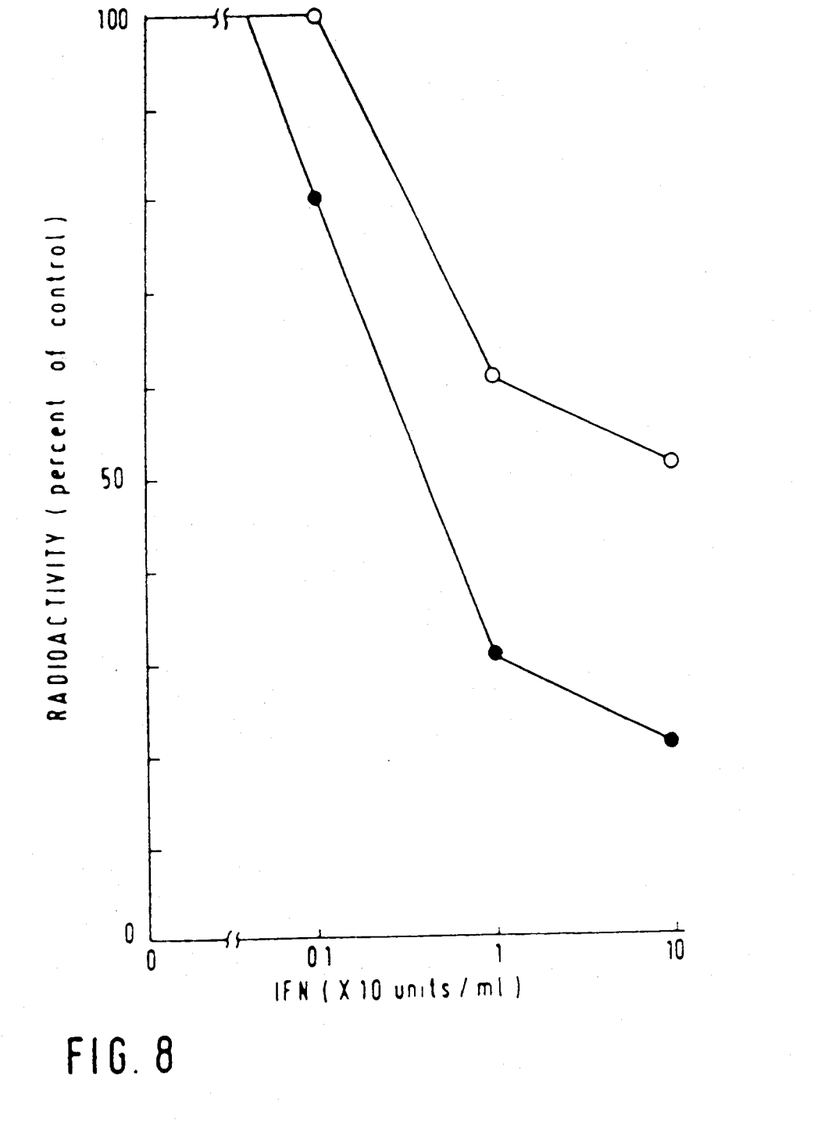
FIG. 8
DNA synthetic activity test in KT cells with [$^3$H] deoxythymidine incorporation into acid-insoluble cell materials 24 hr. after exposure to agents $\bigcirc$ Hu IFN-$\alpha$, $\bullet$ Hu IFN-$\alpha$ and 0.1 $\mu$M dipyridamole.

DNA synthesis in KT cells was inhibited by HuIFN-α and its inhibitory effect was remarkably enhanced by 0.1 μM dipyridamole as shown in FIG. 8.

The results presented here are the first which show the surprising effect of dipyridamole on the anticellular action of HuIFN. As mentioned previously, a synergistic effect of mopidamole, a derivative of dipyridamole, on the antitumor effect of HuIFN has once been reported, but in further publications it was reported that no synergism was found. In a comparative study carried out by the present inventors, the DNA synthesis activity in RSa cells treated with 0.1 μM dipyridamole or mopidamole was inhibited less than with combined treatment with HuIFN-α. When combined with 1. I. unit/ml HuIFN-α DNA synthesis was more strongly depressed as shown in Table 1. The combination dipyridamole/HuIFN-α was significantly more effective than mopidamole/HuIFN-α.

TABLE 1

Comparison of inhibitors effect of DNA synthesis between dipyridamole and mopidamole (% of control)*

| Agent (0.1 μM) | HuIFN-α 0 | (units/ml) 1 |
|---|---|---|
| Non | 100 | 91 |
| Dipyridamole | 92 | 61 |
| Mopidamole | 95 | 84 |

*Logarithmically-growing RSa cells were treated with agents or not for 24 hours, and then labelled with [$^3$H]dTHD, as described in *J. Gen. Virol.* 67:651-661 (1986)

The group of Galavov et al., as mentioned above, reported that dipyridamole induced IFN production. However, the present inventors found no detectable levels of antiviral activity in culture medium of 0.1 μM dipyridamole-treated cells in assay conditions described in *J. Gen. Virol.* 67:651-611 (1986).

The examples below are for illustrative purposes only and are not deemed to limit the scope of the invention.

EXAMPLE 1

Lyophilized preparation containing 2 mg rHuIFN-γ

| | |
|---|---|
| (1) rHuIFN-γ | 2 mg/ml (2 × 10$^6$ I.U.) |
| (2) serum albumin (human) | 10.000 mg/ml |
| (3) NaCl | 1.750 mg/ml |
| (4) mannitol | 40.000 mg/ml |
| (5) polyoxyethylene (20) sorbitanmonooleate | 0.300 mg/ml |
| (6) succinic acid | 2.36 mg/ml |
| (7) 1N NaOH | 36.26 mg/ml |
| (8) water for injection | 1.00 ml |

Preparation

The salts and other additives (2)-(7) are dissolved in ½ of the total required amount of water. The exact amount of HuIFN-γ is then added and the solution is brought to the final required volume by adding the remaining water, filtered through 0.22 82 M filter and filled into vials, lyophilized and stoppered.

EXAMPLE 2

Lyophilized preparation containing 0.03 mg I.U. rHuIFN-α2c

| | |
|---|---|
| (1) rHuIFN-α2c | 0.03 mg (3 × 10⁶ I.U.) |
| (2) isotonic phosphate buffer pH 7 | q.s. |
| (3) human serum albumin | 20.0 mg |
| (4) water for injection | 1.0 ml |

Preparation

Prepared analogously to Example 1.

EXAMPLE 3

Lyophilized preparation containing 1×10⁶ I.U. HuIFN-β

| | |
|---|---|
| (1) rHuIFN-β | 1 × 10⁶ I.U. |
| (2) isotonic phosphate buffer pH7 | q.s. |
| (3) human serum albumin | 20.0 mg |
| (4) water for injection | 1.0 ml |

Preparation

Prepared analogously to Example 1.

EXAMPLE 4

Lyophilized preparation containing 1+10⁶ I.U. rHuIFN-α2

| | |
|---|---|
| (1) IFN-α2 | 1 × 10⁶–3 × 10⁶ I.U. |
| (2) KCl | 0.2 mg |
| (3) Na₂PHO₄·12H₂O | 2.88 mg |
| (4) KH₂PO₄ | 0.2 mg |
| (5) NaCl | 8.0 mg |
| (6) human serum albumin | 20.0 mg |
| (7) water for injection | 1.0 ml |

Preparation

The buffer materials (2), (3), (4), the stabilizer (6), the sodium chloride (5) and the active ingredient (1) were dissolved in the water (7). After sterile filtration, the solution was filled into vials under sterile conditions and freeze dried.

EXAMPLE 5

Lyophilized preparation containing 1-3×10⁶ I.U. rHuIFN-β

| | |
|---|---|
| (1) IFN-β | 1–3 × 10⁶ I.U. |
| (2) KCl | 0.2 mg |
| (3) Na₂HPO₄·12H₂O | 2.88 mg |
| (4) KH₂PO₄ | 0.2 mg |
| (5) NaCl | 8.0 mg |
| (6) human serum albumin | 20.0 mg |
| (7) water for injection | 1.0 ml |

Preparation

Prepared analogously to Example 4.

EXAMPLE 6

Lyophilized preparation containing 1×10⁶–3×10⁶ I.U. rHuIFN-γ

| | |
|---|---|
| (1) IFN-γ | 1 × 10⁶–3 × 10⁶ I.U. |
| (2) Na₂H PO₄·12H₂O | 2.31 mg |
| (3) Na H₂ PO₄2H₂O | 0.55 mg |
| (4) human serum albumin | 1.0 ml |

Preparation

Prepared analogously to Example 4.

EXAMPLE 7

Dragee containing 30 mg dipyridamole

| Composition | |
|---|---|
| (1) Dipyridamole | 30.0 mg |
| (2) lactic acid | 30.0 mg |
| (3) potato starch | 17.5 mg |
| (4) aerosol | 1.5 mg |
| (5) magnesium stearate | 1.0 mg |

(1) +(2) +(3) were mixed and to the mixture was added water to form a moist mass.

The moist mass was passed through a sieve having 1.6 mm spacing and dried at 45° C. in a drying chamber. The dry granules were passed through a sieve having 1 mm spacing and mixed with (4) and (5).

The final mixture was pressed to form dragees.

Core weight : 80 mg

The dragee cores formed were covered by a surface coating in known manner, the coating consisting essentially of sugar and talc. This coating may also contain permitted coloring agents. The finished dragees are polished with wax.

Dragee weight : 120 mg

EXAMPLE 8

| Ampule containing 10 mg dipyridamole | |
|---|---|
| dipyridamole | 10 mg |
| tartaric acid | 4 mg |
| polyethylene glycol | 100 mg |
| hydrochloric acid (1N) to adjust to pH 2.7 | q.s. (~0.018 m) |
| water for injection add. | 2 ml |

The dipyridamole and other ingredients were dissolved in water. After sterile filtration, the solution is filled into ampules and sterilized by heating.

EXAMPLE 9

An ampule from Examples 1 to 6 is formulated for injection using water for injection or isotonic saline solution to provide an injection solution of 2 ml.

EXAMPLE 10

Combination preparation containing dipyridamole and HuIFN

The contents of the ampule from Examples 1 to 6 were reconstituted with the contents of the dipyridamole ampule from Example 8.

The combination preparation of HuIFNα2 and HuIFN-β with dipyridamole was stable at room temperature for about 6 hours. The HuIFN-γ/dipyridamole preparation should be used immediately after reconstitution of the lyophylisate.

EXAMPLE 11

Capsules containing delayed-release dipyridamole formations

30 Kg of rounded tartaric acid started pellets is sprayed, in a special pan, with a suspension consisting of isopropanol, dipyridamole and polyvinylpyrrolidone until the resulting pellets of active substance contain about 45% dipyridamole.

These pellets are sprayed with a lacquer consisting of methacrylic acid/methyl methacrylate copolymer (brand named Eudragit S) and hydroxypropylmethylcellulose phthalate (brand name HP 55) in a weight ratio 85:15 to 50:50.

The organic lacquer solution also contains plasticizer and talc. Two pellet components are sprayed with 5% and 7% of coating and different ratios of lacquer components within the limits specified and are mixed together.

In a special capsule making machine, the quantity of pellets corresponding to 40-25 mg of dipyridamole are packed into an appropriate sized capsules.

We claim:

1. A method of treating tumors capable of being treated with interferon said method comprising contacting said tumors with:
   (a) interferon; and
   (b) dipyridamole, or a pharmaceutically acceptable salt thereof, in an effective amount for enhancing the antitumor effort of interferon.

2. The method of treating tumors of claim 1, wherein said interferon and said dipyridamole are administered simultaneously or substantially simultaneously.

3. The method of treating tumers of claim 1, wherein said interferon is selected from the group of interferons consisting of:
   (a) α-interferon;
   (b) β-interferon; or
   (c) γ-interferon.

4. The method of treating tumors of claim 1, wherein said interferon is administered parenterally.

5. The method of treating tumors of claim 1, wherein said dipyridamole is administered orally.

6. The method of treating tumors of claim 1, wherein said dipyridamole is administered parenterally.

7. The method of treating tumors in claim 1, wherein said dipyridamole is in an accelerated release form.

8. The method of treating tumors in claim 1, wherein said dipyridamole is in a delayed release form.

9. The method of treating tumors in claim 1, wherein said interferon is in a lyophilized form.

10. The method of treating tumors in claim 1, wherein said interferon is mixed with a pharmaceutically acceptable carrier substance.

11. The method of claim 1, wherein said dipyridamole is administered in dosages of 25-100 mg twice daily.

12. A pharmaceutical composition comprising:
    (a) interferon; and
    (b) dipyridamole, or a pharmaceutically acceptable sale thereof, in an amount sufficient for enhancing the anti-tumor affect of said interferon.

13. The pharmaceutical composition of claim 12, wherein said interferon is selected from the group consisting of:
    (a) α-interferon;
    (b) β-interferon; or
    (c) γ-interferon.

14. The pharmaceutical composition of claim 12, wherein said interferon is lyophilized.

15. Teh pharmaceutical composition of claim 12, wherein said interferon is reconstituted with said dipyridamole immediately prior to use.

16. A method for enhancing the tumor-growth inhibitory action of an interferon comprising,
    administering dipyridamole, or a pharmaceutically acceptable salt thereof, in an amount sufficient for enhancing the inhibitory action of said interferon, wherein said interferon and said dipyridamole are simultaneously present at a tumor site.

17. The method of claim 16, wherein said interferon and said dipyridamole are administered simultaneously or substantially simultaneously.

18. The method of claim 16, wherein said interferon is selected from the group of interferons consisting of:
    (a) alpha-interferon;
    (b) beta-interferon; or
    (c) gamma-interferon.

19. The method of claim 16, wherein said dipyridamole is administered in dosages of 25-100 mg twice daily.

20. The method of claim 19, wherein said dipyridamole is administered in dosages of 30-60 mg twice daily.

21. The method of claim 11, wherein said dipyridamole is administered in dosages of 30-60 mg twice daily.

* * * * *